United States Patent
Parkinson et al.

(10) Patent No.: US 7,769,454 B2
(45) Date of Patent: Aug. 3, 2010

(54) POWER MANAGEMENT FOR IMPLANTABLE MEDICAL DEVICE DURING RF COMMUNICATIONS

(75) Inventors: Robert J. Parkinson, Woodbury, MN (US); Kenneth P. Hoyme, Plymouth, MN (US); Scott Vanderlinde, Plymouth, MN (US); Sylvia Quiles, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1039 days.

(21) Appl. No.: 11/275,527

(22) Filed: Jan. 12, 2006

(65) Prior Publication Data

US 2007/0150028 A1 Jun. 28, 2007

Related U.S. Application Data

(63) Continuation-in-part of application No. 11/318,264, filed on Dec. 23, 2005, now abandoned.

(51) Int. Cl.
*A61N 1/08* (2006.01)

(52) U.S. Cl. ...................................................... 607/29

(58) Field of Classification Search ................ 128/903; 600/373, 374, 377, 509, 522, 523; 607/2, 607/4–6, 9, 29–32
See application file for complete search history.

(56) References Cited

U.S. PATENT DOCUMENTS

| | | | |
|---|---|---|---|
| 5,683,432 A * | 11/1997 | Goedeke et al. | 607/32 |
| 6,574,510 B2 | 6/2003 | Von Arx et al. | |
| 6,804,558 B2 * | 10/2004 | Haller et al. | 607/30 |
| 6,993,393 B2 | 1/2006 | Von Arx et al. | |
| 7,406,349 B2 | 7/2008 | Seeberger et al. | |
| 7,539,541 B2 | 5/2009 | Quiles et al. | |
| 2003/0114897 A1 | 6/2003 | Von Arx et al. | |
| 2003/0114898 A1 | 6/2003 | Von Arx et al. | |
| 2003/0149459 A1 | 8/2003 | Von Arx et al. | |
| 2004/0030260 A1 | 2/2004 | Von Arx | |
| 2004/0117204 A1 | 6/2004 | Mazar et al. | |
| 2005/0204134 A1 | 9/2005 | Von Arx et al. | |
| 2005/0240245 A1 | 10/2005 | Bange et al. | |
| 2005/0283208 A1 | 12/2005 | Von Arx et al. | |
| 2006/0030901 A1 | 2/2006 | Quiles et al. | |
| 2006/0030902 A1 | 2/2006 | Quiles et al. | |
| 2006/0030903 A1 | 2/2006 | Seeberger et al. | |
| 2006/0116744 A1 | 6/2006 | Von Arx et al. | |
| 2008/0262573 A1 | 10/2008 | Seeberger et al. | |

FOREIGN PATENT DOCUMENTS

| WO | WO-2005/099817 A1 | 10/2005 |
|---|---|---|
| WO | WO-2006/020546 A1 | 2/2006 |
| WO | WO-2006/020549 A1 | 2/2006 |

* cited by examiner

*Primary Examiner*—Carl H Layno
*Assistant Examiner*—Frances P Oropeza
(74) *Attorney, Agent, or Firm*—Schwegman, Lundberg & Woessner, P.A.

(57) ABSTRACT

In a patient management system, a remote monitoring device interrogates an implantable device on an intermittent basis over a wireless telemetry link, with interrogations being performed either according to a programmed schedule or upon receiving a command to do so via the user interface or the network interface. Described is a system and method for optimizing, limiting, and/or monitoring an implantable device's telemetry usage in order to avoid premature battery depletion and/or raise an alert if excessive battery depletion is beginning to occur.

25 Claims, 3 Drawing Sheets

POWER MANAGEMENT FOR IMPLANTABLE MEDICAL DEVICE DURING RF COMMUNICATIONS

CROSS-REFERENCE TO RELATED APPLICATION(S)

This application is a continuation-in-part of U.S. patent application Ser. No. 11/318,264, filed on Dec. 23, 2005, now abandoned, the specification of which is incorporated herein by reference.

FIELD OF THE INVENTION

This invention pertains to methods and apparatus for medical monitoring.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. If functioning properly, the pacemaker makes up for the heart's inability to pace itself at an appropriate rhythm in order to meet metabolic demand by enforcing a minimum heart rate and/or artificially restoring AV conduction. Implantable devices may also be configured to treat tachyarrhythmias such as fibrillation with electrical stimulation.

As a part of performing their functions in delivering therapy, implantable cardiac devices may equipped with various sensing modalities for detecting cardiac electrical activity as well as measuring other physiological parameters. Other types of implantable medical devices (such as monitoring-only devices or devices for delivering other types of therapy) may also have cardiac or non-cardiac sensing capabilities for acquiring physiological data. The data collected by an implantable medical device can be transmitted over a wireless telemetry link to an external programmer or other external device when the implantable device is interrogated.

SUMMARY

A patient management system may be constructed of an implantable medical device and a remote monitoring device that interrogates and collects data from the implantable device via a wireless telemetry link. Clinical personnel are then able to obtain the data collected by the remote monitoring device for evaluation. The remote monitoring device may be equipped with a network interface for communicating with a patient management server, enabling remotely located clinicians to issue commands to the implantable device and obtain collected data. The remote monitoring device may also have a user interface (e.g., a keyboard and monitor) by which a clinician can communicate commands and obtain collected data.

In a patient management system such as described above, the remote monitoring device interrogates the implantable device on an intermittent basis, with interrogations being performed either according to a programmed schedule or upon receiving a command to do so via the user interface or the network interface. Telemetry is an energy intensive activity for an implantable device which is powered by a battery with a limited life span. Described herein is a system and method for optimizing, limiting, and/or monitoring an implantable device's telemetry usage in order to avoid premature battery depletion and/or raise an alert if excessive battery depletion is beginning to occur.

DETAILED DESCRIPTION

Figure 1:
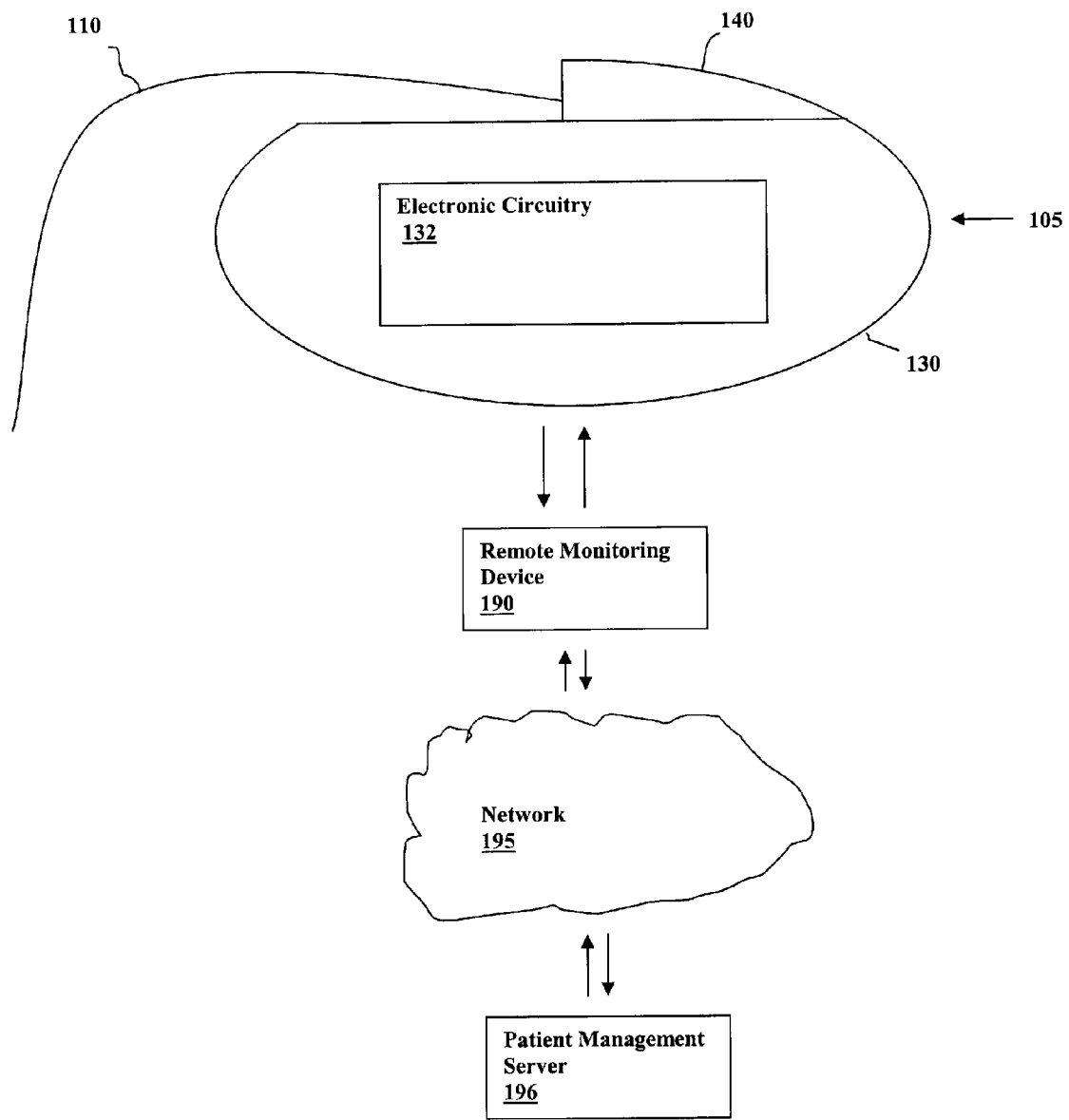
FIG. 1 shows an exemplary patient management system.

A patient management system for monitoring physiological parameters as described herein may be made up of an implantable medical device and a remote monitoring device that communicate with one another over a wireless telemetry link. An example of such an implantable medical device is a cardiac rhythm management device configured to deliver cardiac therapies such as bradycardia pacing, cardioversion/defibrillation therapy, or cardiac resynchronization therapy. Implantable cardiac rhythm management devices such as pacemakers and cardioverter/defibrillators are battery-powered devices which are usually implanted subcutaneously on the patient's chest and connected to electrodes by leads threaded through the vessels of the upper venous system into the heart. FIG. 1 illustrates an implantable medical device 105 that may be, for example, a pacemaker capable of delivering bradycardia and/or anti-tachycardia pacing, an implantable cardioverter/defibrillator, a combination pacemaker/defibrillator, a drug delivery device, or a monitoring-only device. The device has one or more leads 110 with electrodes for disposition in the right atrium, right ventricle, or in a cardiac vein for sensing cardiac activity and/or delivering electrical stimulation to the heart. One or more of the leads 110 may also be adapted for intra-vascular or other disposition in order to provide other types of sensing functionality. The device 105 includes a hermetically sealed housing 130, formed from a conductive metal, such as titanium, which may serve as an electrode for sensing or electrical stimulation. A header 140, which may be formed of an insulating material, is mounted on housing 130 for receiving the leads 110. Contained within the housing 130 is the electronic circuitry 132 for providing the monitoring functionality to the device as described herein and, in the case of a pacemaker or cardioverter/defibrillator, the circuitry for sensing and stimulating the heart. The electronic circuitry 132 includes a controller which may be made up of discrete circuit elements but is preferably a processing element such as a microprocessor together with associated memory for program and data storage which may be programmed to perform algorithms for monitoring physiological parameters or delivering therapy. (As the terms are used herein, "circuitry" and "controller" may refer either to a programmed processor or to dedicated hardware components configured to perform a particular task.) Interfaced to the controller are therapy circuitry for delivering electrical stimulation and sensing circuitry for detecting cardiac activity as well as measuring values of other physiological parameters. For example, the sensing circuitry may include an accelerometer, a minute ventilation sensor, a trans-thoracic impedance sensor, an acoustic sensor, and/or a temperature sensor. Also interfaced to the controller is a telemetry transceiver capable of communicating with an external programmer or a remote monitoring device 190. An external programmer wirelessly communicates with the device 105 and enables a clinician to receive data and modify the programming of the controller. The remote monitoring device 190 similarly communicates with the device 105 and is further interfaced to a network 195 (e.g., an internet connection) for communicating with a patient management server 196 that allows clinical personnel at remote locations to receive data from the remote monitoring device as well as issue commands.

Figure 2:
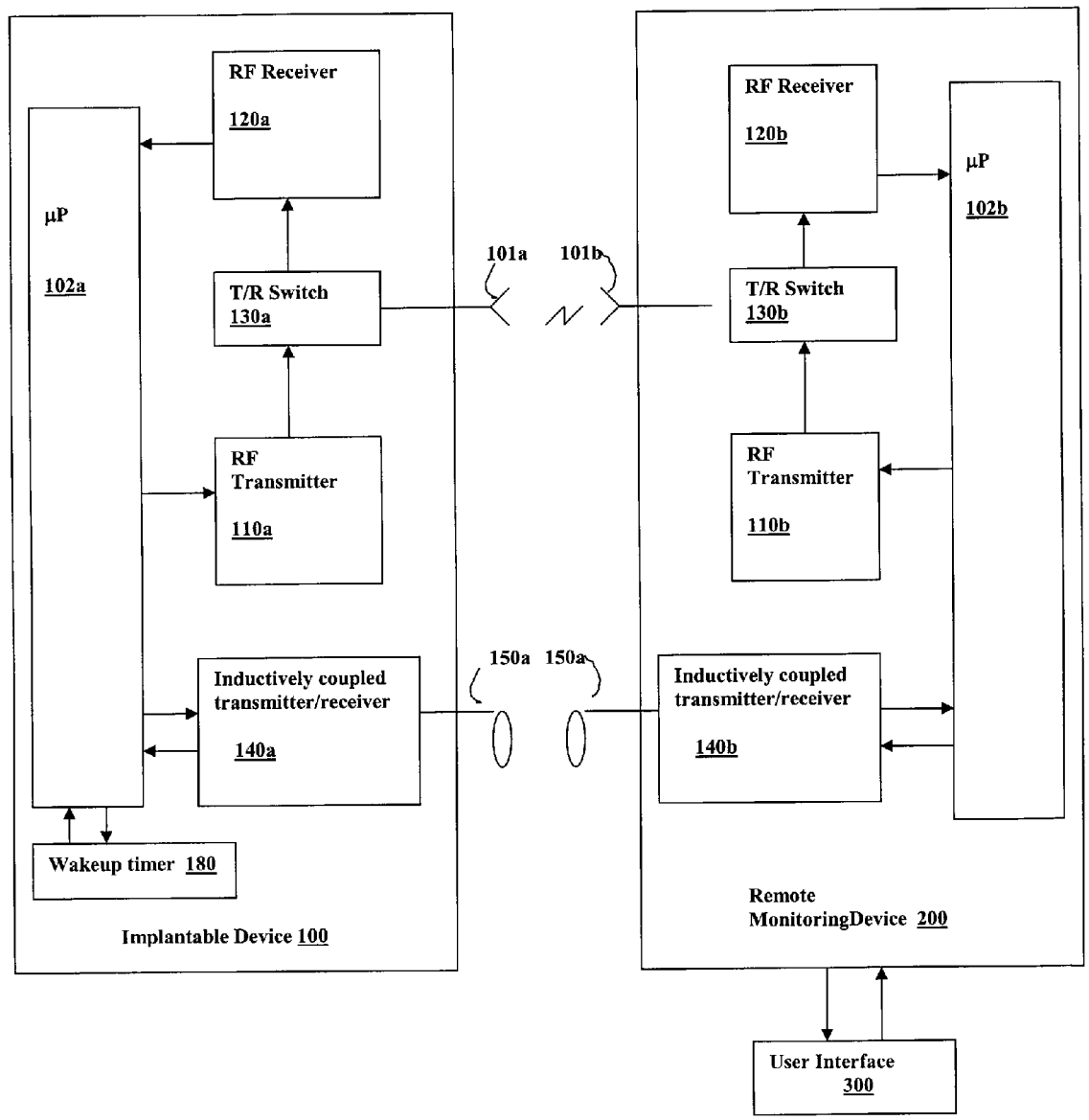
FIG. 2 illustrates the telemetry components of an exemplary remote monitoring device and implantable medical device.

FIG. 2 shows the primary telemetry components of an exemplary remote monitoring device 200 and an implantable medical device 100. In this exemplary embodiment, the external device and the implantable device are microprocessor-based devices each having a controller 102a or 102b that includes a microprocessor and memory for data and program storage that supervises overall device operation as well as telemetry. Code executed by a controller may also implement the power management schemes to be described below.

A long-range RF (radio-frequency) receiver 120a or 120b and a long-range RF transmitter 110a or 110b are interfaced to the microprocessor 102a or 102b in the implantable device and the remote monitoring device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver to establish an RF link. To effect communications between the devices over the RF link, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The RF receiver and transmitter of each device are tunable and may be switched among a plurality of communications channels which differ in frequency. The implantable device also incorporates a means by which the controller can power up or power down the RF receiver and/or transmitter in order to manage duty cycles. A wakeup timer 180 for defining the RF duty cycle is also shown for the implantable device, and this timer can either be implemented in code executed by the controller or can be discrete components. FIG. 2 also shows an inductively coupled transmitter/receiver 140a or 140b and inductive telemetry wands 150a or 150b for the implantable and remote monitoring devices by which wireless communication may take place over an inductive link when the two devices are in close physical proximity to one another. A user interface 300 (e.g., a keyboard and monitor) may be provided as part of the remote monitoring device to enable a user such as a clinician to obtain data from it and direct its operation.

Telemetry use in an implantable medical device requires a significant amount of battery current. This is true for both inductive and RF telemetry but especially so for RF telemetry. Wireless RF communication using far-field radiation can take place over much greater distances than inductive coupling, which makes it possible for a remote monitoring device to communicate with the implantable device as a patient moves about in his or her home. In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. Active transmitters and receivers for this frequency range require special RF components (typically including SiGe or GaAs semiconductor devices) that consume a significant amount of power (typically tens of milliwatts). Implantable medical devices, however, are powered by a battery contained within the housing of the device that can only supply a limited amount of continuous power before it expires. When the battery expires in an implantable device, it must be replaced which necessitates a re-implantation procedure. A remote monitoring device that utilizes RF telemetry for communication thus has the potential to prematurely deplete the battery of an implantable device. Described below are power management schemes that may be implemented in the patient management system for optimizing, limiting, and/or monitoring RF telemetry usage by the implantable device to avoid premature battery depletion and/or raise an alert if excessive battery depletion is beginning to occur.

Optimization of telemetry usage may be obtained by combining scheduled interrogations to more efficiently collect data. A patient management system in which the remote monitoring device communicates with a patient management server allows multiple physicians to schedule interrogations of the implantable device for data collections at the intervals needed by their particular specialization. A user interface may also allow a patient to schedule an interrogation. In one embodiment, the remote monitoring device contains circuitry for: interrogating the implantable medical device over the telemetry link by initiating a communications session and collecting data transmitted from the implantable medical device in accordance with an interrogation schedule; receiving requests to schedule interrogations of the implantable medical device in order to collect specified data; and, combining interrogations scheduled to occur at or near the same time into a single communications session. Combining interrogations in this manner reduces the overall amount of telemetry required to complete the full set of scheduled remote monitoring interrogations.

Telemetry usage by the implantable device may be limited in a number of ways. In one embodiment, the remote monitoring device permits the patient to initiate interrogation of the implanted device via a user interface, and has circuitry for limiting such interrogations to a certain number per week (or other time period) in order to prevent the patient from excessively using telemetry. The remote monitoring device may also have circuitry for receiving a command via a network interface to disable the circuitry for limiting the number of interrogations performed in response to requests received via the user interface to a specified maximum number over a specified period of time.

In another embodiment, the remote monitoring device incorporates circuitry for limiting the time of a communications session for completing one or more scheduled interrogations. The remote monitoring device thus limits the time it tries to complete any single interrogation in order to prevent a telemetry session from remaining open for an extended period of time.

In another embodiment, the remote monitoring device further comprises circuitry for disabling further attempts to initiate a communications session and interrogate the implantable device for a specified period of time after a prior interrogation has been completed. When the remote monitoring device completes an interrogation, it is thus prevented from initiating another for some period of time in order to prevent a failed remote monitoring device from constantly interrogating the implantable device.

There are times when an interrogation begins but cannot finish, such as when the patient walks out of the RF range. In this case, the remote monitoring device may be configured to try to complete the interrogation again at a later time. If this occurs repeatedly, there would be an increased amount of telemetry used in attempting to do an interrogation. In one embodiment, the remote monitoring device has circuitry for repeatedly initiating communications sessions with the implantable device in order to complete a scheduled interrogation and for limiting the number of such repeated initiations. The remote monitoring device thus terminates a scheduled interrogation if the attempt fails a certain number of times, limiting the amount of telemetry that can be used for a given scheduled interrogation.

RF interference generated by various external sources can also make RF telemetry less efficient since it may necessitate repeated transmissions by the implantable device in order to transfer data. To improve the chances of avoiding RF telemetry interference, the remote monitoring device may scan the environment and measure the interference level. Based on this scan, the remote monitoring device could then decide whether to perform the interrogation or delay it until the interference level decreases. In another embodiment, the remote monitoring device includes circuitry for measuring the noise level over the telemetry link and delaying a scheduled interrogation if the measured noise level is above a specified threshold value. The noise level may be measured by first determining that a signal received over the telemetry link does not conform to specified communications protocol (and therefore represents noise) and then measuring the strength of the received signal.

Monitoring of telemetry usage can be accomplished by the remote monitoring device maintaining a record of telemetry use over some specified period of time. Such a record may be derived in a number of ways. First, the implantable device could maintain a count of the total time telemetry has been on while communicating with the remote monitoring device. In one embodiment, the remote monitoring device includes circuitry for maintaining over a specified time period a record of the total time that the telemetry equipment of implantable medical device has been active and for transmitting an alert message via a network interface if the total time exceeds a specified limit value. The record of the total time that the telemetry equipment of implantable medical device has been active may be generated by the remote monitoring device or the implantable device. In the latter instance, the implantable device includes circuitry for maintaining a record of that total time maintained by the implantable medical device that is then transmitted to the remote monitoring device. The remote monitoring device could also estimate the amount of telemetry use based on the amount of data collected. In another embodiment, the remote monitoring device includes circuitry for estimating the record of the total time that the telemetry equipment of implantable medical device has been active from a maintained total of the amount of data collected from the implantable medical device over the specified time period. In each of these telemetry usage monitoring schemes, the telemetry use record may be collected on a regular basis and analyzed to verify it remains within an acceptable range. If the telemetry use is determined to be over the limit a message may be generated to alert technical support personnel or the physician, the situation can then be analyzed to ensure the overuse does not continue over an extended period of time. A check of this can also be programmed into an external programmer in order to warn a physician if an excessive amount of telemetry usage has been experienced by that implanted device.

Figure 3:
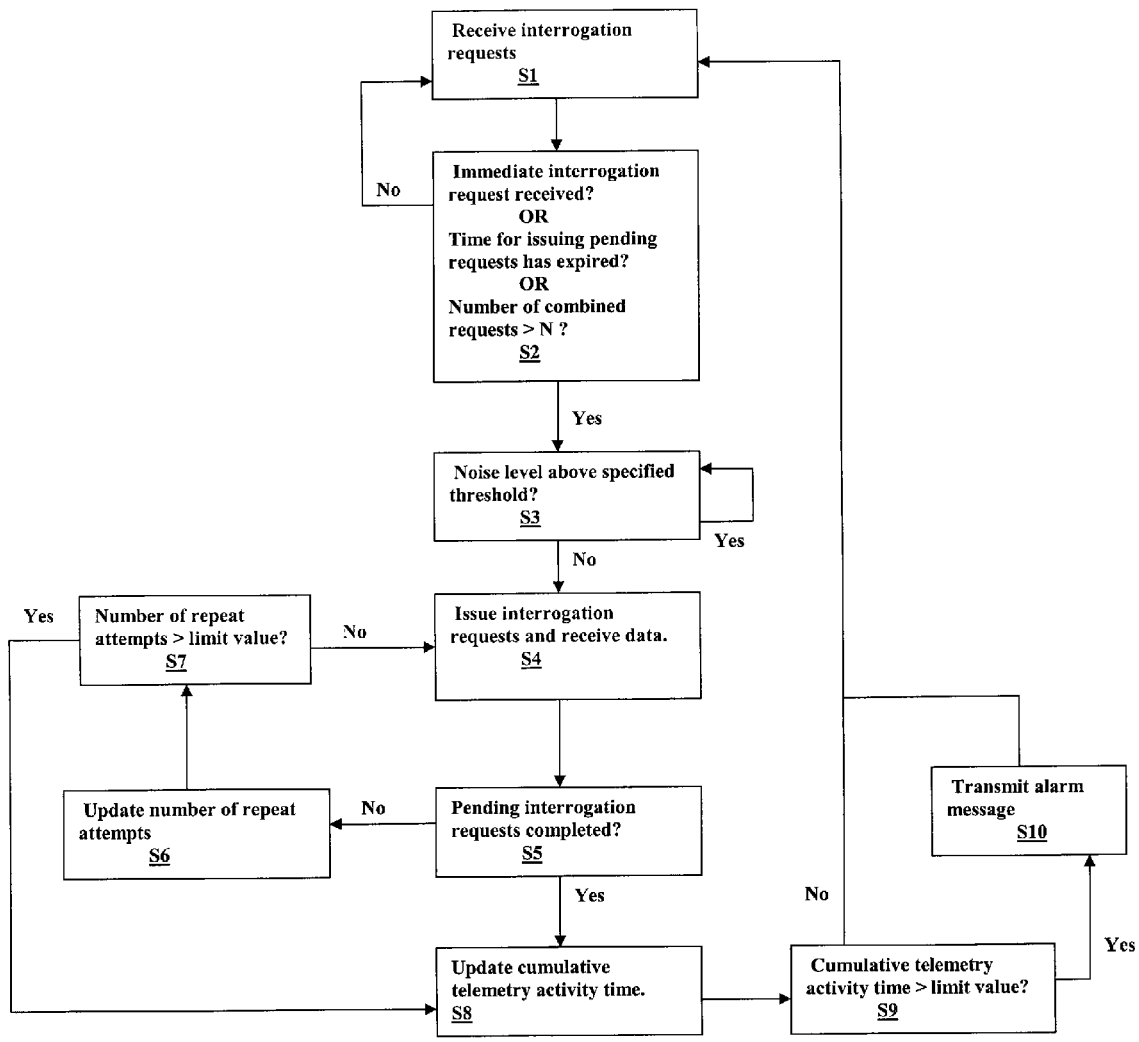
FIG. 3 illustrates an exemplary algorithm that may be performed by a remote monitoring unit.

A system or method in accordance with the present invention may incorporate any or all of the power management techniques discussed above. FIG. 3 illustrates an exemplary algorithm that may be performed by the remote monitoring device that incorporates some of the techniques. At step S1, the remote monitoring device (RMD) receives interrogation requests either from a patient management server via a network interface or from a user (e.g., the patient or a clinician) via a user interface. At step S2, the RMD cumulatively collects the interrogation requests received at step S1 and checks to see if any of the interrogation requests require immediate action, if a specified time limit for issuing pending interrogation requests has expired, or if the number of combined interrogation requests exceeds a specified number N. If none of these conditions are met, the RMD returns to step S1 to collect more interrogation requests. Otherwise, the RMD proceeds to step S3 and measures the noise level of the telemetry link. If the noise level is above a specified threshold, the RMD waits until the noise level falls below that threshold and proceeds to step S4. At step S4, a communications session is established with the implantable device, the pending interrogation requests are issued, and data is received. At step S5, the RMD determines whether or not all of the pending interrogation requests have been completed (i.e., whether all of the data corresponding to the requests has been received). If not, the RMD updates the number of repeat attempts at completing pending interrogation requests at step S6 and compares the number of those repeat attempts at step S7 with a specified repeat limit value. If the repeat limit value is exceeded, the RMD returns to step S1 via step S8. Otherwise, the RMD returns to step S4 and repeats the uncompleted interrogation requests. After all pending interrogation requests have been completed or if the repeat limit value is exceeded at step S7, the RMD updates a cumulative record of the time that telemetry with the implantable device has been active at step S8. The RMD then compares the cumulative telemetry time with a specified limit value at step S9. If the limit value has been exceeded, an alarm message is transmitted via the network interface at step S10. The RMD then returns to step S1 to continue receiving interrogation requests.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A system, comprising:
  a remote monitoring device for an implantable medical device, including
    an interface to a network; and
    circuitry within the remote monitoring device to:
    enable bidirectional wireless communication between the remote monitoring device and the implantable medical device via a telemetry link;
    interrogate the implantable medical device over the telemetry link by initiating a communications session and collecting data transmitted from the implantable medical device in accordance with an interrogation schedule;
    receive requests via the network interface to schedule interrogations of the implantable medical device in order to collect specified data;
    combine interrogations scheduled to occur at or near the same time, as a result of the requests, into a single communications session;
    withhold the combined interrogations until a specified time period for issuing pending requests has expired; and
    override the withholding when a number of received requests satisfies a request number threshold.

2. The system of claim 1 wherein the circuitry within the remote monitoring device for receiving requests to schedule interrogations of the implantable medical device comprises a network interface for receiving requests from a patient management server over a network.

3. The system of claim 1 wherein the circuitry within the remote monitoring device for receiving requests to schedule interrogations of the implantable medical device comprises a user interface that allows a patient or other user to schedule such interrogations.

4. The system of claim 3 wherein the circuitry within the remote monitoring device for receiving requests to schedule interrogations of the implantable medical device further comprises circuitry for limiting the number of interrogations performed in response to requests received via the user interface to a specified maximum number over a specified period of time.

5. The system of claim 4 wherein the remote monitoring device further comprises circuitry for receiving a command via a network interface to disable the circuitry for limiting the number of interrogations performed in response to requests received via the user interface to a specified maximum number over a specified period of time.

6. The system of claim 1 wherein the remote monitoring device further comprises circuitry for limiting the time of a communications session for completing one or more scheduled interrogations.

7. The system of claim 1 wherein the remote monitoring device further comprises circuitry for disabling further attempts to initiate a communications session and interrogate the implantable device for a specified period of time after a prior interrogation has been completed.

8. The system of claim 1 wherein the remote monitoring device further comprises circuitry for repeatedly initiating communications sessions with the implantable device in order to complete a scheduled interrogation and for limiting the number of such repeated initiations.

9. The system of claim 1 wherein the remote monitoring device further comprises circuitry for measuring the noise level over the telemetry link and delaying a scheduled interrogation if the measured noise level is above a specified threshold value.

10. The system of claim 1 wherein the remote monitoring device further comprises circuitry for maintaining over a specified time period a record of the total time that the telemetry equipment of implantable medical device has been active and for transmitting an alert message via a network interface if the total time exceeds a specified limit value.

11. The system of claim 10 wherein the implantable medical device further comprises circuitry for maintaining a record of the total time that the telemetry equipment of implantable medical device has been active and transmitting that record to the remote monitoring device.

12. The system of claim 10 wherein the remote monitoring device further comprises circuitry for maintaining a total of the amount of data collected from the implantable medical device over the specified time period from which a record of the total time that the telemetry equipment of implantable medical device has been active may be estimated.

13. The system of claim 1, wherein the remote monitoring device is configured to communicate with a server via the network interface, and wherein the requests are scheduled on the server by multiple system users.

14. A method by which a remote monitoring device interrogates an implantable medical device over a wireless telemetry link, comprising:

receiving requests via a network to schedule interrogations of the implantable medical device in order to collect specified data;

combining interrogations scheduled to occur at or near the same time into a single communications session;

interrogating the implantable medical device over the telemetry link by initiating a communications session and collecting data transmitted from the implantable medical device in accordance with an interrogation schedule including withholding the combined interrogations until a specified time period for issuing pending requests has expired; and overriding the withholding when a number of received requests satisfies a request number threshold.

15. The method of claim 14 wherein the remote monitoring device receives requests to schedule interrogations of the implantable medical device via a network interface for receiving requests from a patient management server over a network.

16. The method of claim 15 wherein the remote monitoring device receives requests to schedule interrogations of the implantable medical device via a user interface that allows a patient or other user to schedule such interrogations.

17. The method of claim 16 further comprising limiting the number of interrogations performed in response to requests received via the user interface to a specified maximum number over a specified period of time.

18. The method of claim 14 further comprising limiting the time of a communications session for completing one or more scheduled interrogations.

19. The method of claim 14 further comprising disabling further attempts to initiate a communications session and interrogate the implantable device for a specified period of time after a prior interrogation has been completed.

20. The method of claim 14 further comprising repeatedly initiating communications sessions with the implantable device in order to complete a scheduled interrogation and for limiting the number of such repeated initiations.

21. The method of claim 14 further comprising measuring the noise level over the telemetry link and delaying a scheduled interrogation if the measured noise level is above a specified threshold value.

22. The method of claim 14 further comprising maintaining over a specified time period a record of the total time that the telemetry equipment of implantable medical device has been active and for transmitting an alert message via a network interface if the total time exceeds a specified limit value.

23. The method of claim 22 wherein the implantable medical device maintains a record of the total time that the telemetry equipment of implantable medical device has been active and transmits that record to the remote monitoring device.

24. The method of claim 22 further comprising maintaining a total of the amount of data collected from the implantable medical device over the specified time period from which a record of the total time that the telemetry equipment of implantable medical device has been active may be estimated.

25. The method of claim 14, wherein receiving requests via a network to schedule interrogations of the implantable medical device includes receiving requests from multiple users via the network to schedule interrogations of the implantable medical device.

* * * * *